United States Patent
Balthasart et al.

(10) Patent No.: US 7,695,595 B2
(45) Date of Patent: Apr. 13, 2010

(54) PROCESS FOR THE PRODUCTION OF A PURIFIED HYDROFLUOROALKANE, PURIFIED HYDROFLUOROALKANE, USE OF THE HYDROFLUOROALKANE AND METHOD FOR THE ANALYSIS OF A HYDROFLUOROALKANE

(75) Inventors: Dominique Balthasart, Brussels (BE); Charles-Marie Anciaux, Saint-Usage (FR); Yves Mahaut, Sint-Pieters-Leeuw (BE); Roland Klug, Idstein (DE)

(73) Assignee: Solvay S.A., Brussels (BE)

( * ) Notice: Subject to any disclaimer, the term of this patent is extended or adjusted under 35 U.S.C. 154(b) by 179 days.

(21) Appl. No.: 11/410,706

(22) Filed: Apr. 25, 2006

(65) Prior Publication Data

US 2006/0185972 A1    Aug. 24, 2006

Related U.S. Application Data

(62) Division of application No. 10/221,014, filed as application No. PCT/EP01/02806 on Mar. 7, 2001, now Pat. No. 7,077,960.

(30) Foreign Application Priority Data

Mar. 7, 2000    (FR) .................................. 00 02944

(51) Int. Cl.
  *B01D 3/36* (2006.01)
  *C01B 7/19* (2006.01)
(52) U.S. Cl. .............................. 203/74; 203/77; 203/80; 570/178
(58) Field of Classification Search .................. 203/2, 203/3, 50, 67, 74, 77, 80; 570/178
  See application file for complete search history.

(56) References Cited

U.S. PATENT DOCUMENTS

| | | | | |
|---|---|---|---|---|
| 3,660,254 A | * | 5/1972 | Dunn | ......................... 205/460 |
| 4,507,555 A | | 3/1985 | Chang | |
| 4,870,213 A | | 9/1989 | Inbasekaran et al. | |
| 5,198,199 A | * | 3/1993 | LaCroix et al. | ............... 423/88 |
| 5,211,020 A | * | 5/1993 | Taylor et al. | ................... 62/630 |
| 5,276,223 A | * | 1/1994 | Ohno et al. | ................. 570/164 |
| 5,328,571 A | | 7/1994 | Millauer | |
| 5,336,817 A | | 8/1994 | Eicher et al. | |
| 5,345,015 A | * | 9/1994 | Ohno et al. | ................. 570/164 |
| 5,621,147 A | | 4/1997 | Yokokoji et al. | |
| 5,654,494 A | * | 8/1997 | Tung et al. | ................. 570/169 |
| 5,703,359 A | | 12/1997 | Wampler, III | |
| 5,824,225 A | | 10/1998 | Powell et al. | |

(Continued)

FOREIGN PATENT DOCUMENTS

EP    0467531 A1    1/1992

(Continued)

OTHER PUBLICATIONS

Mikes, Laboratory Handbook of Chromatographic and Allied Methods, John Wiley, pp. 540-541 (1979).

*Primary Examiner*—Ernest G Therkorn
(74) *Attorney, Agent, or Firm*—Connolly Bove Lodge & Hutz LLP

(57) ABSTRACT

Process for the production of a hydrofluoroalkane, according to which hydrofluoroalkane comprising organic impurities is subjected to at least two distillations.

12 Claims, 1 Drawing Sheet

U.S. PATENT DOCUMENTS

| | | | |
|---|---|---|---|
| 5,872,010 A | 2/1999 | Karger et al. | |
| 5,920,068 A | 7/1999 | Marsh | |
| 5,968,368 A | 10/1999 | Powell et al. | |
| 6,328,907 B1 * | 12/2001 | Nakada et al. | 252/67 |
| 6,437,201 B1 | 8/2002 | Ewing et al. | |
| 6,646,253 B1 | 11/2003 | Rohwer et al. | |
| 6,863,780 B2 * | 3/2005 | Nakada et al. | 203/50 |
| 7,077,960 B2 * | 7/2006 | Balthasart et al. | 210/635 |
| 2003/0191350 A1 * | 10/2003 | Ohno et al. | 570/105 |
| 2004/0015022 A1 * | 1/2004 | Ohno et al. | 570/164 |
| 2004/0158109 A1 * | 8/2004 | Ohno et al. | 570/134 |
| 2005/0159632 A1 * | 7/2005 | Ohno et al. | 570/163 |
| 2006/0185972 A1 * | 8/2006 | Balthasart et al. | 203/71 |

FOREIGN PATENT DOCUMENTS

| | | |
|---|---|---|
| WO | WO 95/24370 A1 | 9/1995 |
| WO | WO 99/50208 A1 | 10/1999 |

\* cited by examiner

PROCESS FOR THE PRODUCTION OF A PURIFIED HYDROFLUOROALKANE, PURIFIED HYDROFLUOROALKANE, USE OF THE HYDROFLUOROALKANE AND METHOD FOR THE ANALYSIS OF A HYDROFLUOROALKANE

RELATED APPLICATIONS

This application is a division of application Ser. No. 10/221,014, filed Jan. 28, 2003, now U.S. Pat. No. 7,077,960 which is a 371 of PCT/EP01/02806, filed Mar. 7, 2001, which claims benefit to French Application No. 00.02944, filed Mar. 7, 2000.

A subject-matter of the present invention is a process for the production of a purified hydrofluoroalkane, a purified hydrofluoroalkane, the use of the hydrofluoroalkane and a method for the analysis of a hydrofluoroalkane.

Some hydrofluoroalkanes, such as in particular 1,1,1,2-tetrafluorethane and 1,1,1,2,3,3,3-heptafluoropropane, can be used, because of their physical properties and of their favourable toxicology, in pharmaceutical applications, in particular as propellent gas in medical aerosols.

The industrial production of such hydrofluoroalkanes provides, however, a product which comprises saturated and unsaturated impurities. As these impurities are often toxic, strict standards are likely to be adopted, limiting the content, for example, of olefinic impurities to less than 5 ppm by volume (see, for example, the draft standard of the FDA (Food and Drug Administration, Center for Drug and Evaluation and Research, October 1998) relating to the content of the said impurities in 1,1,1,2-tetrafluoroethane for MDI products).

Consequently, it is necessary to purify the hydrofluoroalkane of industrial grade in order to obtain a product of pharmaceutical grade. It is also necessary to have available analytical methods which make it possible to detect and to identify traces of unsaturated and saturated organic impurities in the hydrofluoroalkane. This presents problems, in particular when these impurities have a boiling point close to that of the hydrofluoroalkane.

Patent Application WO-A-90/8750 relates to a process for the purification of 1,1,1,2-tetrafluoroethane from olefinic impurities, according to which the 1,1,1,2-tetrafluoroethane is subjected to catalytic hydrogenation. According to this known process, contents ranging up to 10 ppm of a single olefinic impurity, namely 1,1-difluoro-2-chloroethylene, are observed. According to the patent application, the detection limit for 1,1-difluoro-2-chloroethylene is 10 ppm. Furthermore, this known process does not make possible satisfactory purification from all the saturated and unsaturated organic impurities. In particular, this known process does not make it possible to remove 1,1,2,2-tetrafluoroethane (HFC-134). The presence of substantial amounts of HFC-134 in 1,1,1,2-tetrafluoroethane for pharmaceutical applications is not desirable since its toxicity has not been examined to any extent.

It was consequently desirable to have available an efficient manufacturing process which makes possible access to a purified hydrofluoroalkane, preferably of pharmaceutical grade. It was particularly desirable-to have available a manufacturing process which makes possible an efficient reduction in the content of each individual organic impurity while achieving very low overall contents of organic impurities.

The invention consequently relates to a process for the production of a purified hydrofluoroalkane, according to which the hydrofluoroalkane, comprising organic impurities, is subjected to at least two distillations, the second distillation being carried out at a pressure greater than that of the first distillation, and at least one fraction composed of hydrofluoroalkane purified from organic impurities is recovered at the outlet of the second distillation. Generally, this fraction can be used directly for pharmaceutical applications. However, the process according to the invention does not rule out one or more additional finishing stages.

The process according to the invention is particularly well suited to the production of a purified hydrofluoroalkane which can be used for pharmaceutical applications.

In a first alternative form of the process according to the invention, the heavy impurities are separated from the hydrofluoroalkane in the first distillation and the light impurities are separated from the hydrofluoroalkane in the second distillation.

In a second alternative form of the process according to the invention, which alternative form is preferred, the light impurities are separated from the hydrofluoroalkane in the first distillation and the heavy impurities are separated from the hydrofluoroalkane in the second distillation. In this case, the fraction composed of hydrofluoroalkane purified from organic impurities is recovered at the top of the second distillation.

The term "light impurity" is understood to denote an impurity exhibiting, at the pressure of the distillation, a boiling point lower than that of the hydrofluoroalkane. The term "heavy impurity" is understood to denote an impurity exhibiting, at the pressure of the distillation, a boiling point greater than that of the hydrofluoroalkane.

It has been found, surprisingly, that the process according to the invention makes possible an extremely efficient purification of hydrofluoroalkane from saturated and unsaturated organic impurities, thus providing hydrofluoroalkane exhibiting a low content of the said organic impurities, in particular as regards its content of saturated impurities and, if appropriate, of (chloro)fluoroethenes and (chloro)fluoropropenes.

The process according to the invention applies to any hydrofluoroalkane. It applies in particular to the hydrofluoroalkanes capable of being used in pharmaceutical applications. Mention may be made, for example, of hydrofluoroethanes, hydrofluoropropanes and hydrofluorobutanes preferably exhibiting a low toxicity towards man. Specific examples of such hydrofluoroalkanes are 1,1,1,2-tetrafluoroethane, 1,1,1,2,3,3,3-heptafluoropropane, 1,1,1,3,3-pentafluoropropane and 1,1,1,3,3-pentafluorobutane. Among these hydrofluoroalkanes, the process according to the invention applies preferably to 1,1,1,2-tetrafluoroethane and to 1,1,1,2,3,3,3-heptafluoropropane. The process according to the invention applies in a very particularly preferred way to the production of 1,1,1,2-tetrafluoroethane of pharmaceutical grade.

The pressure in the first distillation is generally less than 10 bar absolute. It is often at most 9 bar. It is preferably at most 8 bar. The pressure in the first distillation is generally at least 1 bar. It is often at least 1.5 bar. It is preferably at least 2 bar.

The pressure in the second distillation is generally greater than 10 bar absolute. It is often at least 12 bar. It is preferably at least 15 bar. In a particularly preferred way, it is at least 17 bar. In a very particularly preferred way, it is at least 19 bar. The pressure in the second distillation is generally at most 40 bar. It is often at most 30 bar. It is preferably at most 25 bar.

In the present description, any reference to the pressure corresponds to the absolute pressure measured at the top of the distillation column.

The temperature at which the first or the second distillation is carried out corresponds approximately to the boiling point of the hydrofluoroalkane at the pressure chosen for the respective distillation.

Each of the two distillations can be carried out in one or more distillation columns. Use will preferably be made of a single column per distillation.

The distillation columns which can be used in the process according to the invention are known per se. Use may be made, for example, of conventional plate columns or plate columns of dual-flow type or alternatively of columns with bulk or structured packing.

The number of theoretical plates in the first distillation is generally at least 10. It is often at least 15. A number of at least 20 gives good results.

The number of theoretical plates in the second distillation is generally at least 20. It is often at least 30. A number of at least 40 gives good results.

The molar reflux ratio in the first distillation is generally at least 50.

The molar reflux ratio in the second distillation is generally at least 5.

It has been found that the process according to the invention makes possible an extremely efficient purification of the hydrofluoroalkane from saturated and unsaturated organic impurities, thus providing hydrofluoroalkane exhibiting a low content of the said organic impurities, in particular as regards, if appropriate, its content of (chloro)fluoroethenes, of (chloro)fluoropropenes and of saturated impurities. This is because the process according to the invention makes possible the production of a hydrofluoroalkane in which the content of each individual organic impurity has been greatly reduced.

The invention consequently also relates to a hydrofluoroalkane exhibiting an individual content of each organic impurity of less than 10 molar ppm. This individual content is preferably at most 8 ppm. In a particularly preferred way, this individual content is at most 5 ppm. An individual content of at most 2.8 ppm is very particularly preferred. An individual content of at most 1 ppm is even more preferred.

The contents of impurities in the hydrofluoroalkane according to the invention can advantageously be determined according to the method described in Example 4. The hydrofluoroalkane according to the invention can preferably be used for pharmaceutical applications.

The total content of organic impurities in the hydrofluoroalkane according to the invention is generally at most 200 molar ppm. This total content is often at most 100 ppm. The total content is more often at most 50 ppm. The total content is preferably at most 30 ppm. In a particularly preferred way, the total content is at most 25 ppm. A total content of at most 20 ppm is even more preferred. The total content can even be at most 5 ppm.

The total content of unsaturated organic impurities in the hydrofluoroalkane according to the invention is generally at most 5 molar ppm. This content is often at most 3 ppm. The content is more often at most 2 ppm. The content is preferably at most 1.8 ppm. In a particularly preferred way, the content is at most 1.7 ppm.

Hydrofluoroalkane is preferably 1,1,1,2-tetrafluoroethane.

The content of fluoropropenes determined in the 1,1,1,2-tetrafluoroethane according to the invention is generally less than 1.4 molar ppm. This content is often at most 1.2 ppm. The content is more often at most 1.0 ppm. The content is preferably at most 0.9 ppm. In a particularly preferred way, the content is at most 0.8 ppm.

The content of 1,1,2,2-tetrafluoroethane in the 1,1,1,2-tetrafluoroethane according to the invention is generally less than 10 molar ppm. The content is preferably at most 8 ppm. In a particularly preferred way, the content is at most 5 ppm. In an even more preferred way, the content is at most 2 ppm.

The invention also relates to a method for the analysis of the content of organic impurities in a hydrofluoroalkane, in which method
(a) the hydrofluoroalkane is subjected to a chromatography operation and;
(b) an operation is carried out in which the organic impurities are detected by mass spectrometry.

The method according to the invention makes it possible, surprisingly, to determine, in a single analytical operation, the nature and the amount of a large number of organic impurities present in a hydrofluoroalkane. The method according to the invention even makes it possible to carry out a quantitative detection of several organic impurities exhibiting between them the same retention time in the chromatography operation. In a particularly surprising way, the method according to the invention also makes possible the quantitative detection of impurities which exhibit the same retention time in the chromatography operation as the hydrofluoroalkane.

It has also been found that HCFC-124(1,1,1,2-tetrafluoro-2-chloroethane), which is an impurity which may be present in 1,1,1,2,3,3,3-heptafluoropropane and which could not be determined simultaneously with other organic impurities prior to the present invention, can be analysed in the same operation with the other organic impurities by virtue of the method according to the invention.

The chromatography operation is preferably a gas chromatography operation.

The stationary phase in the chromatography operation is generally nonpolar. A polymer of polysiloxane type is often employed as stationary phase. A stationary phase composed of optionally cross linked polydimethylsiloxane has given good results. In the case of gas chromatography, good results have been obtained with an Rtx®-1 gas chromatography column sold by Restek Corp.

In an alternative form, the stationary phase exhibits moderate polarity. Such a stationary phase can be composed, for example, of a mixture of nonpolar polymer as described above with a polar polymer. Such polar polymers are chosen, for example, from polymers functionalized by polar groups, in particular from functionalized polyolefins or polyalkylsiloxanes. The polar group can be chosen, for example, from hydroxyl, ether, ester, phenoxy and, preferably, from nitrile. A polysiloxane of general formula

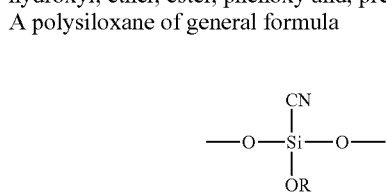

in which R is a $C_1$ to $C_4$ alkyl group, preferably a methyl group, is particularly preferred as polar polymer. In the alternative form described above, the content of polar polymer is generally greater than or equal to 1% by weight of the stationary phase. This content is often greater than or equal to 2% by weight. It is preferably greater than or equal to approximately 5% by weight. The content of polar polymer is generally less than or equal to 15% by weight of the stationary phase. The content is often less than or equal to 10% by weight. It is preferably less than or equal to approximately 8% by weight.

The initial temperature of the chromatography operation is generally adjusted at the most to 40° C. This temperature is often adjusted at the most to 0° C. This temperature is more often adjusted at the most to −20° C. This temperature is preferably adjusted at the most to −40° C. As a general rule, it is at least −80° C.

In the chromatography operation, there is generally at least one stage with a constant temperature gradient which provides a controlled temperature rise starting from the initial temperature. This temperature gradient is generally at least 0.1° C./min. It is preferably at least 0.5° C./min.

The temperature gradient is generally at most 10° C./min. It is preferably at most 2° C./min.

The column is preferably a capillary column. The length of the column is generally at most 200 m. The length is often at most 120 m. The length of the column is generally at least 20 m.

The injection can be carried out in split or splitless mode. Injection in split mode is preferred.

The carrier gas is often chosen from helium and hydrogen. Helium is preferred.

The internal diameter of the column is generally at most 0.32 mm. The diameter is often at most 0.25 mm. The diameter is preferably at most 0.20 mm. The internal diameter of the column is often at least 0.10 mm. The diameter is preferably at least 0.15 mm.

The thickness of the stationary phase film deposited inside the column is generally at least 0.5 µm. The thickness is preferably greater than or equal to approximately 1 µm. The thickness of the stationary phase film deposited inside the column is generally at most 5 µm.

A specific alternative form of the method according to the invention applies preferably when the internal diameter and the thickness of the film lie within the preferred ranges.

The length of the column is, in this alternative form, advantageously at least 30 m. In a more particularly preferred way, it is greater than or equal to approximately 40 m. The length of the column is advantageously at most 100 m. In a more particularly preferred way, it is less than or equal to approximately 60 m.

In this alternative form, the temperature gradient as defined above is generally at least 10° C./min. It is preferably at least 20° C./min. In a more particularly preferred way, the gradient is greater than or equal to approximately 40° C./min. The temperature gradient in this alternative form is generally at most 50° C./min.

The initial temperature in this alternative form is generally at most −10° C. It is preferably less than or equal to −20° C. The initial temperature in this alternative form is generally at least −50° C.

This alternative form of the method according to the invention makes it possible, surprisingly, to further accelerate the analytical operation while retaining the other advantages of the method according to the invention, in particular with respect to the simultaneous detection and determination of the organic impurities.

Premanufactured gas chromatography columns which make it possible to implement the method according to the invention are available commercially, for example Rtx®-624 from Restec and DB®-624 from J & W.

Detection by mass spectrometry is preferably carried out using the selected ion monitoring (SIM) technique.

According to another preferred alternative form, detection by mass spectrometry is carried out using the time-of-flight (TOF) technique. Mass spectrometers for detection by using the-time-of-flight technique, which are preferred in the method according to the invention, make it possible to record a high number of mass spectra per second, namely approximately 1 to 500, preferably 100 to 500, spectra per second. Spectrometers which can be used for the implementation of the method according to the invention are, for example, those sold by Leco Corporation under the name Pegasus® II and those sold by Thermoquest under the name Tempus™.

The hydrofluoroalkanes for which the content of organic impurities can be analysed by the method according to the invention are the same as those obtained according to the process according to the invention. The method according to the invention applies, preferably, to the analysis of 1,1,1,2-tetrafluoroethane or of 1,1,1,2,3,3,3-heptafluoropropane. It applies in particular to the analysis of 1,1,1,2-tetrafluoroethane.

The method according to the invention is particularly efficient as determination of the content of all the organic impurities can be obtained by a single analytical operation. That being the case, only this operation has to be validated, that is to say standardized and confirmed. Consequently, the calibration possibly needed between the analysis of various samples is simplified.

The method according to the invention makes it possible to achieve a very short duration necessary for the analysis, which can typically be carried out in less than two hours, often in less than one hour. A complete analysis of the impurities can be arrived at in a time of approximately 10 minutes. This efficiency makes it possible in particular to improve the performance of industrial manufacturing processes requiring control of the quality of a hydrofluoroalkane. This is because it is possible to meet, with greater flexibility and speed, urgent orders for hydrofluoroalkane and reduce the hydrofluoroalkane storage times.

The invention consequently also relates to a process for the manufacture of a hydrofluoroalkane comprising the use of the analytical method according to the invention for controlling the quality of the hydrofluoroalkane.

In an alternative form, the hydrofluoroalkane is a purified hydrofluoroalkane. In this alternative form, the process for the manufacture of a hydrofluoroalkane often comprises a purification stage. This process preferably comprises (a) the use of the method according to the invention for the analysis of a crude hydrofluoroalkane;

(b) a purification of the crude hydrofluoroalkane in order to obtain a purified hydrofluoroalkane;

(c) and a second use of the method according to the invention for the analysis of the purified hydrofluoroalkane.

If appropriate, the purification can be carried out, for example, according to the production process according to the invention. The process for manufacturing a hydrofluoroalkane according to the invention preferably applies to the hydrofluoroalkanes mentioned above.

The invention also relates to a process for the manufacture of a pharmaceutical aerosol, comprising at least one hydrofluoroalkane of pharmaceutical grade, comprising the use of the analytical method according to the invention for controlling the quality of the hydrofluoroalkane of pharmaceutical grade.

The process for the manufacture of a pharmaceutical aerosol according to the invention is particularly suitable for the manufacture of a pharmaceutical aerosol for inhalation comprising at least one hydrofluoroalkane liquefied under pressure and a medicament. The medicament is preferably present in the form of a powder in the suspended state. The hydrofluoroalkane is present as propellent gas.

The process for the manufacture of a pharmaceutical aerosol is particularly advantageous as the analytical method makes it possible to carry out, in a particularly efficient way, the strict quality control laid down for pharmaceutical applications.

The invention also relates to the use of the hydrofluoroalkane according to the invention as propellent gas in pharmaceutical aerosols.

The invention also relates to the use of the hydrofluoroalkane according to the invention in the electronics industry.

DESCRIPTION OF THE PREFERRED EMBODIMENTS

Figure 1:
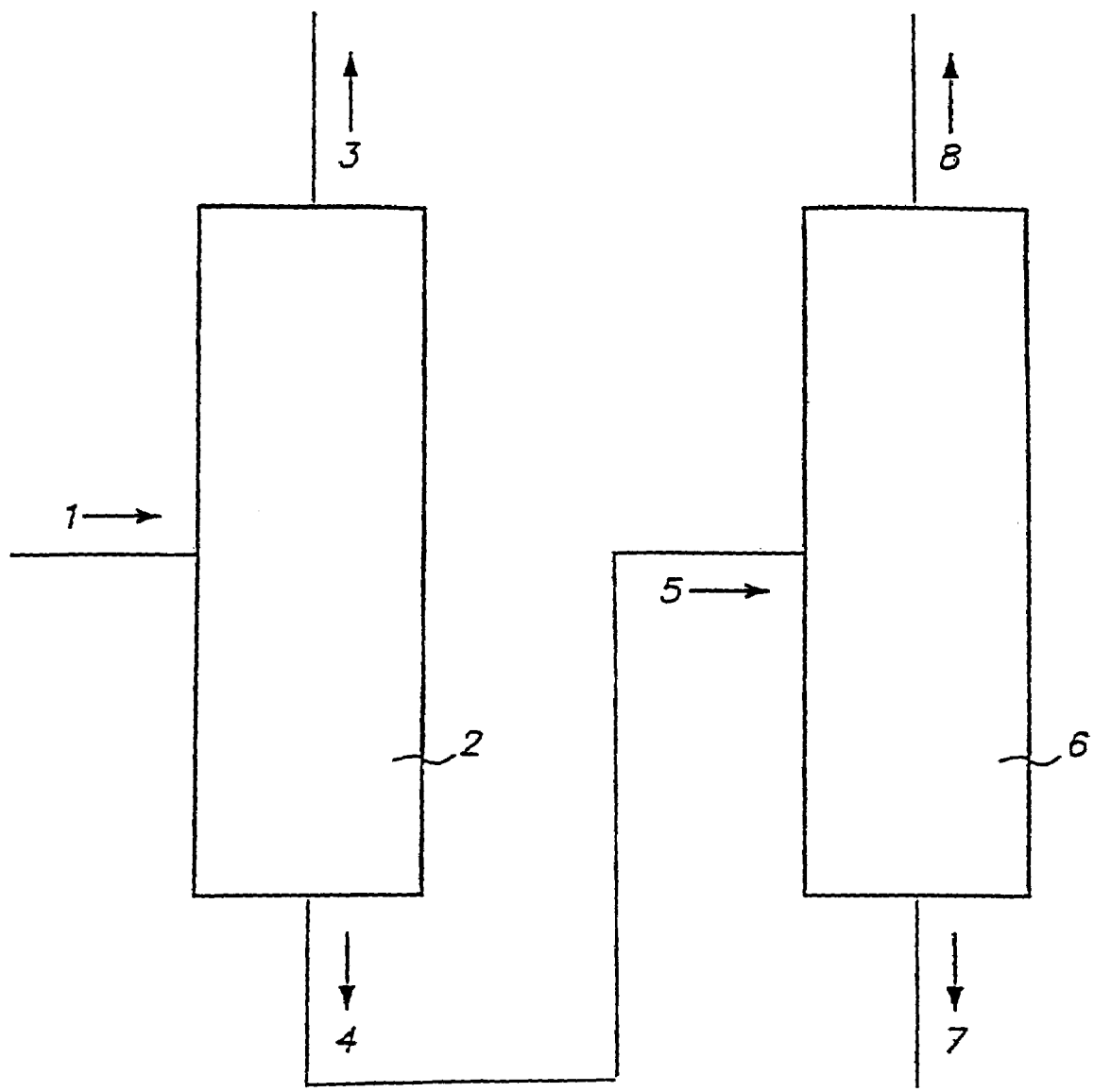
FIG. 1 represents a diagram of a plant which can be used for implementing the preferred alternative form of the production process according to the invention.

FIG. 1 represents a diagram of a plant which can be used for implementing the preferred alternative form of the production process according to the invention. The numbers refer to FIG. 1. The hydrofluoroalkane comprising organic impurities is introduced via route (1) into a first distillation column (2). At the top (3) of this column (2), a fraction is obtained comprising light impurities (lower but similar boiling point) and those which form a minimum-boiling azeotrope at this pressure. At the bottom (4) of this column (2), a fraction is obtained comprising hydrofluoroalkane with a reduced content of other impurities, which fraction is introduced via route (5) into the second distillation column (6) operating at a higher pressure than the column (2). At the bottom (7) of the second column (6), a fraction is recovered which is enriched in heavy impurities which exhibit a higher boiling point with respect to that of the hydrofluoroalkane. At the top (8) of the second column (6), hydrofluoroalkane is obtained which is purified from organic impurities.

The examples given below are intended to illustrate, without implied limitation, the process, the analytical method and a hydrofluoroalkane according to the invention.

EXAMPLE 1

In Accordance With The Invention

An impure 1,1,1,2-tetrafluoroethane fraction comprising 57.2 molar ppm of saturated organic impurities and 10.6 molar ppm of unsaturated organic impurities was employed. This fraction was introduced at the level of the 7th theoretical plate into a first distillation column comprising 20 theoretical plates. The pressure in the first column was 6.75 bar abs. A reflux ratio of 250 was provided. A fraction was withdrawn at the top corresponding to 10% of the feed and comprising 51.4 molar ppm of saturated organic impurities and 3.9 molar ppm of unsaturated organic impurities. A fraction was recovered at the bottom composed of 1,1,1,2-tetrafluoroethane and purified from "light" impurities comprising 41.5 molar ppm of saturated organic impurities and 34.9 molar ppm of unsaturated organic impurities, which fraction was introduced at the level of the 13th plate into a second distillation column comprising 20 theoretical plates. The pressure in this second distillation column was 19.3 bar absolute. A reflux ratio of 14.8 was provided. At the column bottom, 10% of the feed of the first column, comprising 320 molar ppm of saturated organic impurities and 9.8 molar ppm of unsaturated organic impurities was withdrawn. A fraction was withdrawn at the top of this column composed of 1,1,1,2-tetrafluoroethane purified from heavy impurities comprising 10.7 molar ppm of saturated organic impurities and 1.3 molar ppm of unsaturated organic impurities.

EXAMPLE 2

Not In Accordance With The Invention

An impure 1,1,1,2-tetrafluoroethane fraction comprising 2 750 molar ppm of saturated organic impurities and 75 molar ppm of unsaturated organic impurities was employed. This fraction was, introduced at the level of the 14th theoretical plate into a first distillation column comprising 20 theoretical plates. The pressure in the first column was 13 bar abs. A reflux ratio of 50 was provided. A fraction was withdrawn at the top corresponding to 10% of the feed and comprising 1 950 molar ppm of saturated organic impurities and 150 molar ppm of unsaturated organic impurities. A fraction was recovered at the bottom composed of 1,1,1,2-tetrafluoroethane purified from "light" impurities comprising 2 950 molar ppm of saturated organic impurities and 40 ppm of unsaturated organic impurities, which fraction was introduced at the level of the 14th plate into a second distillation column comprising 20 theoretical plates. The pressure in this second distillation column was 12 bar absolute. A reflux ratio of 12.5 was provided. At the column bottom, 10% of the feed of the first column, comprising 15 500 molar ppm of saturated organic impurities and 50 molar ppm of unsaturated organic impurities, was withdrawn. A fraction was withdrawn at the top of this column composed of 1,1,1,2-tetrafluoroethane purified from heavy impurities comprising 275 molar ppm of saturated organic impurities and 31 molar ppm of unsaturated organic impurities.

EXAMPLE 3

Not In Accordance With The Invention

An impure 1,1,1,2-tetrafluoroethane fraction, comprising 2 950 molar ppm of saturated organic impurities and 50 molar ppm of unsaturated organic impurities, was employed. This factor was introduced at the level of the 14th-theoretical plate into a first distillation column comprising 20 theoretical plates. The pressure in the first column was 7.5 bar abs. A reflux ratio of 50 was provided. A fraction was withdrawn at the top corresponding to 10% of the feed and comprising 1 830 molar ppm of saturated organic impurities and 200 molar ppm of unsaturated organic impurities. A fraction was recovered at the bottom composed of 1,1,1,2-tetrafluoroethane purified from "light" impurities comprising 3 200 molar ppm of saturated organic impurities and 32 ppm of unsaturated organic impurities, which fraction was introduced at the level of the 14th plate into a second distillation column comprising 20 theoretical plates. The pressure in this second distillation column was 6.5 bar absolute. A reflux ratio of 12.5 was provided. At the column bottom, 10% of the feed of the first column, comprising 27 500 molar ppm of saturated organic impurities and 50 molar ppm of unsaturated organic impurities, was withdrawn. At the top of this column, a fraction was withdrawn composed of 1,1,1,2-tetrafluoroethane purified from heavy impurities comprising 200 molar ppm of saturated organic impurities and 28 molar ppm of unsaturated organic impurities.

EXAMPLE 4

An analysis of 1,1,1,2-tetrafluoroethane of pharmaceutical grade obtained according to a production process in accordance with the invention was carried out. To do this, gas chromatography was carried out on an Rtx®-1 gas chromatography column sold by Restek Corp. comprising, as stationary phase, 100% of dimethylpolysiloxane crosslinked by the Crossbond® process. The dimensions of the column were 105m×0.25mm×1.0 micron. A temperature programme comprising 2 stages was used, the first beginning at −50° C., and the temperature was raised at a rate of 1° C./min to a temperature of 0° C. Subsequently, in a second stage, the temperature was raised at a rate of 10° C./min to 250° C. Detection was carried out by mass spectrometry with the selected ion monitoring (SIM) technique using an HP 5972 mass spectrometer sold by Hewlett-Packard. Standardization was carried out by employing a gas standard mixture composed of 10 ppm of each impurity to be analysed.

The contents of various impurities in the 1,1,1,2-tetrafluoroethane according to the invention and in the crude 1,1,1,2-tetrafluoroethane which is employed in the process according to the invention are shown in the table below. The detection limit of the analytical method according to the invention is also shown. This detection limit was validated by random calibration with respect to 5 concentrations of 1 to 10 ppm of each individual impurity. The values obtained were corrected according to the purity of each of the impurities present in the calibration mixture.

The table also includes the values contained in the draft FDA standard mentioned above. All the values are expressed in molar ppm, apart from the "Assay" value, which is expressed as a percent. An empty box means that the impurity in question was not observed.

| Organic impurity | Formula | Detection limit of the method according to the invention | Draft FDA standard | Crude HFC-134a | HFC-134A Invention |
|---|---|---|---|---|---|
| HFC-23 | $CHF_3$ | 0.2 | 5 | | |
| CFC-13 | $CClF_3$ | 0.3 | 5 | < | |
| HFC-32 | $CH_2F_2$ | 0.2 | 5 | | |
| HFC-125 | $CHF_2$—$CF_3$ | 0.3 | 5 | 50 | |
| HFC-143a | $CH_3$—$CF_3$ | 0.4 | 10 | 124 | |
| CFC-115 | $CClF_2$—$CF_3$ | 0.2 | 5 | 0.3 | |
| HFC-1123 | $CHF$=$CF_2$ | 0.2 | 5 | | |
| c/t-HFC-1318my | $CF_3$—$CF$=$CF$—$CF_3$ | 0.7 | 5 | | |
| t/c-HFC-1318my (1) | $CF_3$—$CF$=$CF$—$CF_3$ | 0.3 | 5 | < | < |
| HFC-245cb | $CF_3$—$CF_2$—$CH_3$ | 0.2 | 5 | 0.3 | |
| HFC-1234yf | $CH_2$=$CF$—$CF_3$ | 0.3 | 5 | 1.3 | |
| HFC-134 | $CHF_2$—$CHF_2$ | 0.4 | 1 000 | 2 824 | < |
| HFC-152a | $CH_3$—$CHF_2$ | 0.2 | 300 | 1.3 | |
| HFC-217ba | $CF_3$—$CClF$—$CF_3$ | 0.5 | 5* | 2.4 | 0.5 |
| HFC-161 | $CH_3$—$CH_2F$ | 0.2 | 30 | | |
| HFC-1225ye | $CHF$=$CF$—$CF_3$ | 0.2 | 5 | 1.8 | |
| HFC-1243zf | $CH_2$=$CH$—$CF_3$ | 0.4 | 5 | 7.3 | 0.9 |
| HFC-1132 | $CHF$=$CHF$ | 0.4 | 5 | < | |
| $C_3H_2F_4$ (2) | | 0.3 | 5* | 11.8 | |
| HCFC-22 | $CHClF_2$ | 0.2 | 50 | 0.2 | |
| HFC-1336mzz | $CF_3$—$CH$=$CH$—$CF_3$ | 0.5 | 5 | | |
| CFC-12 | $CCl_2F_2$ | 0.2 | 100 | 0.2 | |
| HCC-40 | $CH_3Cl$ | 0.4 | 5 | 4.0 | |
| HCFC-124a | $CHF_2$—$CClF_2$ | 0.2 | 5 | | |
| HCFC-124 | $CHClF$—$CF_3$ | 0.4 | 100 | 36 | |
| HCFC-1122 | $CHCl$=$CF_2$ | 0.3 | 5 | 28 | 0.3 |
| HCFC-31 | $CH_2ClF$ | 0.4 | 5 | 0.4 | |
| CFC-114 | $CClF_2$—$CClF_2$ | 0.1 | 5 | | |
| CFC-114a | $CCl_2F$—$CF_3$ | 0.1 | 25 | 19 | |
| HFC-152 | $CH_2F$—$CH_2F$ | 0.5 | 5 | | |
| c/t-HCFC-1122a (3) | $CHF$=$CClF$ | 0.3 | 5* | 4.6 | |
| c/t-HCFC-1122a (3) | $CHF$=$CClF$ | 0.3 | 5* | < | |
| HCFC-133a | $CH_2Cl$—$CF_3$ | 0.4 | 5 | 0.4 | |
| trans-HCFC-1131 | $CHCl$=$CHF$ | 0.5 | 5* | 10.3 | 0.2 |
| cis-HCFC-1131 | $CHCl$=$CHF$ | 0.5 | 5* | | |
| CFC-12B1 | $CClBrF_2$ | 0.2 | 5 | | |
| CFC-1112a | $CF_2$=$CCl_2$ | 0.3 | 5 | | |
| HCFC-123 | $CHCl_2$—$CF_3$ | 0.4 | 5 | | |
| CFC-11 | $CCl_3F$ | 0.3 | 5 | | |
| HCFC-123a | $CHClF$—$CClF_2$ | 0.3 | 5 | | |
| c/t-HCFC-1121 | $CHCl$=$CClF$ | 0.2 | 5 | | |
| HCC-30 | $CH_2Cl_2$ | 0.6 | 5* | < | |
| HCFC-132b | $CClF_2$—$CH_2Cl$ | 0.6 | 5 | | |
| CFC-113 | $CClF_2$—$CCl_2F$ | 0.4 | 5 | | |

| Organic impurity | Formula | Detection limit of the method according to the invention | Draft FDA standard | Crude HFC-134a | HFC-134A Invention |
|---|---|---|---|---|---|
| HCC-1120 | CHCl=CCl$_2$ | 0.8 | 5* | < | < |
| Sum of organic impurities | | | 1 000 | 3 127.6 | 1.9 |
| Sum of olefins | | | 5 | 65.1 | 1.4 |
| Assay | | | 99.9% | | 100% |

< below the detection limit
The impurities for which the content is below the detection limit were not taken into consideration in calculating the sums of impurities.
(1) Estimated value
(2) Value calculated by taking into consideration the response factor of HFC-1234yf
(3) E/Z isomers, value calculated by taking into consideration the response factor of HCFC-1122
*Compound not mentioned individually in the draft FDA standard.

It is apparent that the 1,1,2,2-tetrafluoroethane according to the invention, obtained in accordance with the process according to the invention, exhibits a content of organic impurities which is extremely low and far below the values of the draft FDA standard. Furthermore, no individual organic impurity has a content exceeding 1 molar ppm.

It is also apparent that the method according to the invention makes it possible to detect and to identify, with an extremely high sensitivity, all the impurities included in the draft FDA standard.

The invention claimed is:

1. A process for the production of purified 1,1,1,2-tetrafluoroethane according to which 1,1,1,2-tetrafluoroethane, comprising olefinic impurities, is subjected to at least two distillations, the second distillation being carried out at a pressure greater than that of the first distillation, wherein the pressure in the first distillation is less than 10 bar and the pressure in the second distillation is at least 10 bar, and at least one fraction comprising 1,1,1,2-tetrafluoroethane of pharmaceutical quality containing less than 5 molar ppm of olefinic impurities is recovered at the outlet of the second distillation.

2. The process according to claim 1, in which the pressure in the first distillation is at most 9 bar.

3. The process according to claim 2, in which the pressure in the first distillation is at most 8 bar.

4. The process according to claim 1, in which the pressure in the second distillation is at least 15 bar.

5. The process according to claim 1, in which the fraction composed of 1,1,1,2-tetrafluoroethane purified from olefinic impurities is recovered at the top of the second distillation.

6. A process for the production of purified 1,1,1,2-tetrafluoroethane according to which 1,1,1,2-tetrafluoroethane, comprising olefinic impurities, is subjected to at least two distillations, the second distillation being carried out at a pressure greater than that of the first distillation, wherein the pressure in the first distillation is less than 10 bar and the pressure in the second distillation is at least 19 bar, and at least one fraction comprising 1,1,1,2-tetrafluoroethane of pharmaceutical quality containing less than 5 molar ppm of olefinic impurities is recovered at the outlet of the second distillation.

7. A process for the production of purified 1,1,1,2-tetrafluoroethane of pharmaceutical quality, according to which 1,1,1,2-tetrafluoroethane, comprising olefinic impurities, is subjected to at least two distillations, the second distillation being carried out at a pressure greater than that of the first distillation, wherein the pressure in the first distillation is less than 10 bar and the pressure in the second distillation is at least 10 bar, and at least one fraction composed of 1,1,1,2-tetrafluoroethane of pharmaceutical quality containing less than 5 molar ppm of olefinic impurities is recovered at the outlet of the second distillation.

8. The process according to claim 7, in which the pressure in the first distillation is at most 9 bar.

9. The process according to claim 8, in which the pressure in the first distillation is at most 8 bar.

10. The process according to claim 7, in which the pressure in the second distillation is at least 15 bar.

11. The process according to claim 10, in which the pressure in the second distillation is at least 19 bar.

12. The process according to claim 7, in which the fraction composed of 1,1,1,2-tetrafluoroethane purified from olefinic impurities is recovered at the top of the second distillation.

* * * * *